(12) United States Patent
Kyba et al.

(10) Patent No.: US 11,306,287 B1
(45) Date of Patent: Apr. 19, 2022

(54) METHOD OF GENERATING SKELETAL MUSCLE STEM CELLS FROM PLURIPOTENT CELLS

(71) Applicant: Regents of the University of Minnesota, Minneapolis, MN (US)

(72) Inventors: Michael Kyba, St. Paul, MN (US); Sun Kin Sunny Chan, St. Paul, MN (US); Robert W. Arpke, St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 550 days.

(21) Appl. No.: 15/625,619

(22) Filed: Jun. 16, 2017

Related U.S. Application Data (60) Provisional application No. 62/351,135, filed on Jun. 16, 2016.

(51) Int. Cl.
| | | |
|---|---|---|
| *C12N 5/074* | (2010.01) | |
| *A61K 35/34* | (2015.01) | |
| *A61K 48/00* | (2006.01) | |

(52) U.S. Cl.
CPC ............ *C12N 5/0607* (2013.01); *A61K 35/34* (2013.01); *A61K 48/00* (2013.01); *C12N 2501/105* (2013.01)

(58) Field of Classification Search
CPC ............ C12N 5/0607; C12N 2501/105; A61K 35/34; A61K 48/00
See application file for complete search history.

(56) References Cited

U.S. PATENT DOCUMENTS

| | | | | |
|---|---|---|---|---|
| 2007/0155013 A1* | 7/2007 | Akaike | ................ | C12N 5/0606 435/455 |
| 2010/0055167 A1 | 3/2010 | Zhang et al. | | |
| 2012/0141441 A1* | 6/2012 | Calos | ................... | C12N 5/0696 424/93.21 |
| 2015/0166961 A1 | 6/2015 | Parker et al. | | |

OTHER PUBLICATIONS

"U.S. Appl. No. 15/625,782, Final Office Action dated Sep. 3, 2019", 10 pgs.
"U.S. Appl. No. 15/625,782, Non Final Office Action dated Mar. 5, 2019", 11 pgs.
"U.S. Appl. No. 15/625,782, Response filed May 28, 2019 to Non Final Office Action dated Mar. 5, 2019", 6 pgs.
Tdesco, Francesco Saverio, et ai., "Repairing skeletal muscle: regenerative potential of skeletal muscle stem cells", JCI The Journal of Clinical Investigation, (2010), 11-19.
Charville, Gregory' W., "Ex Vivo Expansion and In Vivo Self-Renewal of Human Muscle Stem Cells", Stem Cell Reports, 5(4), (2015), 621-632.
Xu, Xiaoti, "Human Satellite Cell Transplantation and Regeneration from Diverse Skeletal Muscles", Stem Cell Reports, 5(3), (2015), 419-434.
"U.S. Appl. No. 15/625,782, Restriction Requirement dated Dec. 4, 2018", 7 pgs.
"U.S. Appl. No. 15/625,782, Response filed Dec. 31, 2018 to Restriction Requirement dated Dec. 4, 2018", 4 pgs.
"U.S. Appl. No. 15/625,782, Response filed Mar. 8, 2021 to Final Office Action dated Jan. 14, 2021".
Chan Sunny Sun-Kin, "Skeletal Muscle Stem Cells from PSC-Derived Teratomas Have Functional Regenerative Capacity", Cell Stem Cell, 23, (2018), 74-85.
Incitti, Tania, et al., "Pluripotent stem cell-derived myogenic progenitors remodel their molecular signature upon in vivo engraftment". Proc. Natl. Acad. Sci. USA, 116(10), (2019), 4346-4351.
Lin, Caorui, et al., "Glycine Enhances Satellite Ceil Proliferation, Cell Transplantation, and Oligonucleotide Ef?cacy in Dystrophic Muscle", Molecular Therapy, 28(5), (May 2020), 1339-1358.
"U.S. Appl. No. 15/625,782, Advisory Action dated Mar. 18, 2021", 3 pgs.
"U.S. Appl. No. 15/625,782, Advisory Action dated May 7, 2021", 4 pgs.
"U.S. Appl. No. 15/625,782, Non-Final Office Action dated Nov. 22, 2021", 20 pgs.
"U.S. Appl. No. 15/625,782, Response filed Apr. 14, 2021 to Advisory Action dated Mar. 18, 2021", 10 pgs.
"U.S. Appl. No. 15/625,782, Response filed May 12, 2021 to Advisory Action dated May 7, 2021", 9 pgs.
Geller, Anne, et al., "The Role of Membrane Bound Complement Regulatory Proteins in Tumor Development and Cancer Immunotherapy", *Frontiers in Immunology*, 10: Article 1074, (May 2019), 1-13.
Jovanovic, Bojana, et al., "Transforming growth factor beta receptor type III is a tumor promoter in mesenchymal stem like triple negative breast cancer", *Breast Cancer Research*, 16: R69, (2014), 14 pgs.
Lang, Liwei, et al., "Fibroblast Growth Factor Receptor 4 Targeting in Cancer: New Insights into Mechanisms and Therapeutic Strategies", *Cells, 8, 31*, (2019), 13 pgs.
Lee, Mi-Ok, et al., "Inhibition of pluripotent stem cell-derived teratoma formation by small molecules", *Proc. Natl. Acad. Sci. USA, 110(35)*, (Aug. 2013), E3281-E3290.
Tan, Kezhe, et al., "CD73 Expression on Mesenchymal Stem Cells Dictates the Reparative Properties via its Anti-Inflammatory Activity", *Hindawi Stem Cells International, vol. 2019, Article ID 8717694*, (2019), 12 pgs.
Uezumi, Aklyoshi, et al., "Cell-Surface Protein Profiling Identifies Distinctive Markers of Progenitor Cells in Human Skeletal Muscle", *Stem Cell Reports, vol. 7*, (2016), 263-278.
Wang, Yuzi Zin, et al., "Muscle Stem Cells at a Glance", *J. Cell Sci: 127(21)*, (Nov. 1, 2014), 4543-4548.

\* cited by examiner

*Primary Examiner* — Blaine Lankford
(74) *Attorney, Agent, or Firm* — Schwegman Lundberg & Woessner, P.A.

(57) ABSTRACT

Compositions and methods of the invention are directed to the formation and use of teratoma-derived skeletal muscle stem cells. In one embodiment, the teratoma-derived skeletal muscle stem cells improve muscle contractile force (definition "functional") when administered to a patient in need thereof.

4 Claims, 6 Drawing Sheets

METHOD OF GENERATING SKELETAL MUSCLE STEM CELLS FROM PLURIPOTENT CELLS

PRIORITY

This application claims the benefit of priority from U.S. Provisional Patent Application Ser. No. 62/351,135, filed on Jun. 16, 2016, which is herein incorporated in its entirety by reference.

GOVERNMENT GRANT SUPPORT

This invention was made with government support under R01 NS083549 awarded by the National Institutes of Health. The government has certain rights in the invention.

BACKGROUND OF THE INVENTION

Muscle stem cells express the transcription factor PAX7 and are the primary cell type responsible for regeneration of muscle after injury and maintenance throughout life (Gunther et al., 2013; Seale et al., 2000; von Maltzahn et al., 2013). Muscle stem cells are rare in adult muscle, comprising only 1-2% of the mononuclear fraction (Bosnakovski et al., 2008). Satellite cells in normal healthy muscle reside under the fiber basal lamina (Mauro, 1961), and methods of isolation require the muscle tissue containing them to be removed from the donor, therefore in humans, only relatively small biopsies are possible. Satellite cells have considerable regenerative potential (Arpke et al., 2013; Collins et al., 2005; Hall et al., 2010; Sacco et al., 2008), however the small cell number that can be isolated from a biopsy is not sufficient to enable the regeneration of a significant amount of muscle. Although satellite cells will divide and their progeny will proliferate when placed into in vitro culture, these cultured cells are no longer the same as satellite cells, and their transplantation potential is very limited (Gussoni et al. 1992; Mendell et al., 1995; Montarras et al. 2005; Sacco et al. 2008). Embryonic stem (ES) cells and induced pluripotent stem (iPS) cells have been considered as a source of material for muscle cell transplantation, however they are difficult to differentiate into muscle in vitro and although some protocols have been published to derive skeletal myotubes from pluripotent cells in vitro (Chal et al., 2015; Shelton et al., 2014), transplantable cells that can give rise to meaningful muscle grafts, i.e. grafts capable of generating a measurable difference in force produced have only been derived from pluripotent cells that have been genetically modified to overexpress PAX3 (Darabi et al., 2008; Filareto et al., 2013) or PAX7 (Darabi et al., 2012).

SUMMARY OF INVENTION

Herein, it is shown that skeletal muscle stem cells with regenerative potential can be isolated from pluripotent stem cells by differentiating such stem cells in teratomas in an immunodeficient host animal. In the mouse system, it is shown that the skeletal muscle stem cells within teratomas can be isolated using the surface markers α7-Integrin+ and VCAM-1+ in combination with negativity for the surface markers CD45 and CD31. When these cells are transplanted into the diseased muscle of an mdx mouse (a mouse model for the human disease Duchenne muscular dystrophy), teratoma derived myogenic progenitors demonstrate unprecedented/surprising engraftment potential. When transplanted into the tibialis anterior muscle, 40,000 cells can reconstitute 70-80% of the muscle volume. The new fibers are functional, i.e. the transplanted muscles can produce much greater absolute force compared to controls, and they improve specific force and reduce fatigability, two features of dystrophic muscle. The teratoma derived muscle progenitors also give rise to a population of PAX7+ muscle stem cells, which plays a role in long-term maintenance of the skeletal muscle. Outside of genetic modification with Pax3 or Pax7, no publication to date has demonstrated a method of producing skeletal muscle stem cells from pluripotent stem cells with these properties which endow therapeutic potential (i.e. this level of muscle output per cell input, any improvement in force generation of transplanted muscle compared to control, and reconstitution of the satellite cell compartment of transplanted muscle—three qualities which together play a role in viable cell therapy for skeletal muscle regeneration/repair).

Together the results demonstrate that teratomas are a rich and accessible source of therapeutically useful skeletal muscle stem cells.

One embodiment provides a teratoma derived skeletal muscle stem cell that is Lin–α7-integrin+ VCAM1+ (α7+ VCAM+). Another embodiment provides a teratoma derived skeletal muscle stem cell that is CD45-neg CD31-neg VCAM1+ Itga7+ or CD45-neg CD31-neg CD56+.

One embodiment provides a method to prepare teratoma derived skeletal muscle stem cells comprising: a) generate a teratoma in an immunodeficient animal, b) harvest the teratoma 1-2 months later; and c) isolate skeletal muscle stem cells. In one embodiment, the immune deficient animal is an immunodeficient mouse or pig. In another embodiment, the skeletal muscle stem cells are isolated using surface markers for positive and/or negative selection. In one embodiment, the surface markers comprise CD45-neg CD31-neg VCAM1+ Itga7+. In another embodiment, the surface markers comprise CD45-neg CD31-neg CD56+. In one embodiment, the surface marker comprises CD56+. In one embodiment, the surface markers comprise CD9+, CD29+, CD46+, CD73-, CD82+ or a combination thereof.

One embodiment provides a method to treat a muscle disease or disorder or damaged muscle tissue comprising administering to subject in need thereof an effective amount of teratoma derived muscle cells. In one embodiment, the muscle stem cells are skeletal muscle stem cells. In one embodiment the muscle stem cell is Lin– α7-integrin+ VCAM1+(α7+ VCAM+). In another embodiment, the muscle stem cell is CD45-neg CD31-neg VCAM1+ Itga7+ or CD45-neg CD31-neg CD56+. In one embodiment, the muscle stem cell is CD56+. In one embodiment, the muscle stem cell is CD9+, CD29+, CD46+, CD73-, CD82+ or a combination thereof. In one embodiment, the muscle disease or disorder or damaged muscle tissue is a result of injury or overuse, a genetic disorder, cancer, inflammation, infection or medical treatment. In one embodiment, the genetic disorder is muscular dystrophy. In one embodiment, the administered muscle stem cells improve muscle contractile force as compared to muscle contractile force before muscle stem cell administration.

One embodiment provides a method to prepare a composition comprising mixing an effective therapeutic amount of teratoma derived muscle stem cells with a pharmaceutically acceptable carrier. Another embodiment provides for use of teratoma derived muscle stem cells to prepare a medicament for treating muscle tissue suffering from a disease, disorder or damage. In one embodiment, the disease, disorder or damage is a result of injury or overuse, a genetic disorder, cancer, inflammation, infection or medical treatment.

One embodiment provides an isolated skeletal muscle stem cell that is produced by injecting cells with the potential to form one or more teratomas into a recipient animal, allowing one or more teratomas to form, and then harvesting cells from the one or more teratomas.

One embodiment provides an isolated teratoma derived skeletal muscle stem cell that is CD9+, CD29+, CD46+, CD73−, CD82+ or a combination thereof.

DETAILED DESCRIPTION OF THE INVENTION

Figure 1A:
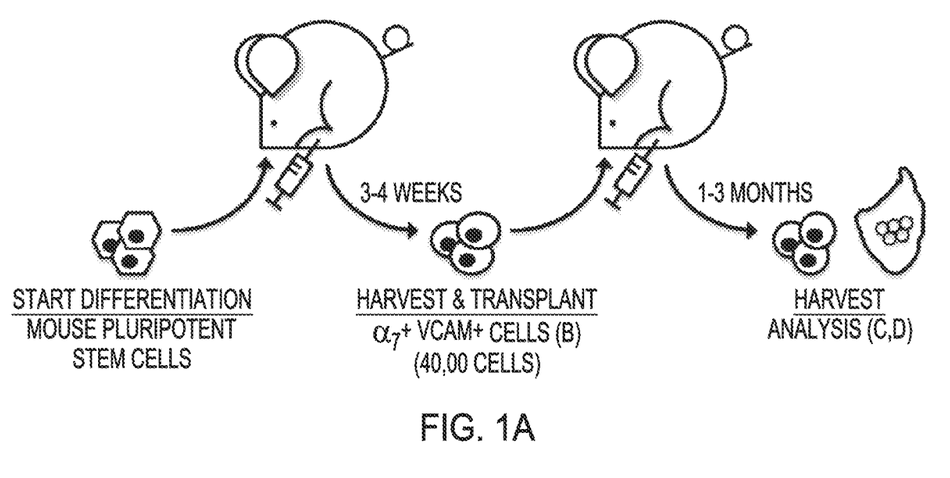
FIGS. 1A-G. Generation of skeletal myogenic progenitors/stem cells from mouse pluripotent stem cells. (A) Schematic of generating skeletal myogenic progenitors/stem cells from mouse pluripotent stem cells. (B, C) FACS profiling of 3 week-old teratomas revealed the presence of CD31−CD45−α7+ VCAM+ putative myogenic progenitors. Immunostaining confirmed their myogenic identity (myosin heavy chain+, Pax7+). (D-G) Teratoma-derived α7+ VCAM+ myogenic progenitors/stem cells engrafted and differentiated into functional muscle fibers. (D) Engraftment (dystrophin+fibers) at 1 month (left) and 3 months (right). The whole tibialis anterior muscle is outlined. (E-G) Ex vivo physiological assessment revealed functional improvement at 3 months after α7+ VCAM+ cells transplantation (n=6 biological replicates). *p<0.05, p<0.01, *p<0.001 versus PBS (vehicle).
Figure 1B:
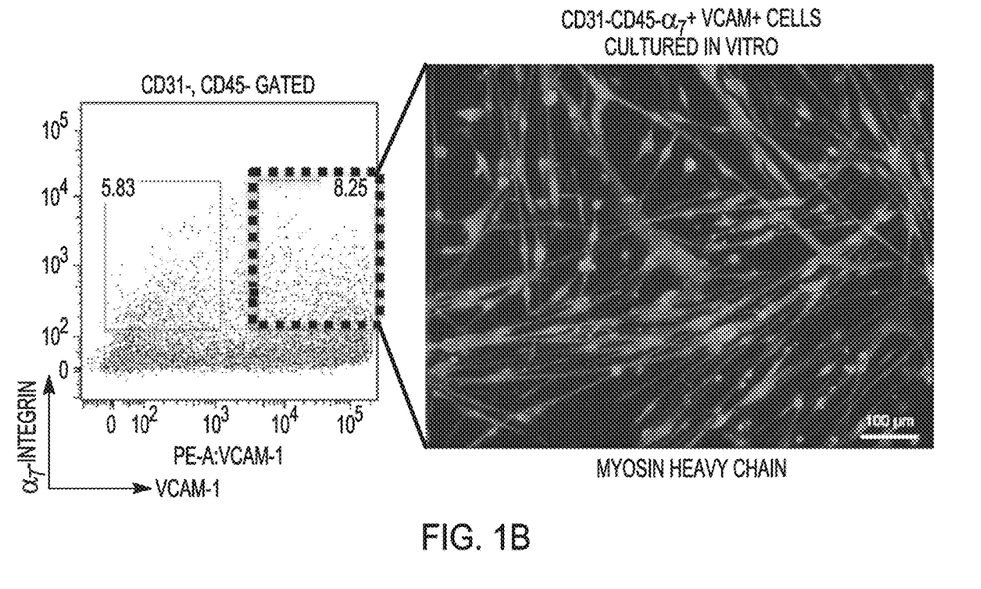
Figure 1C:
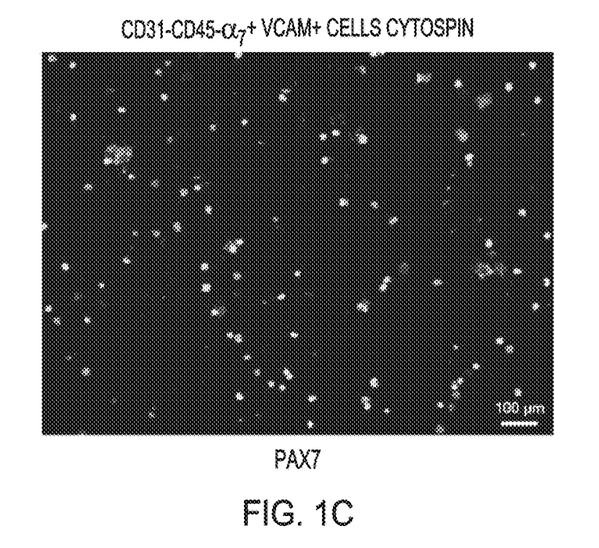
Figure 1D:
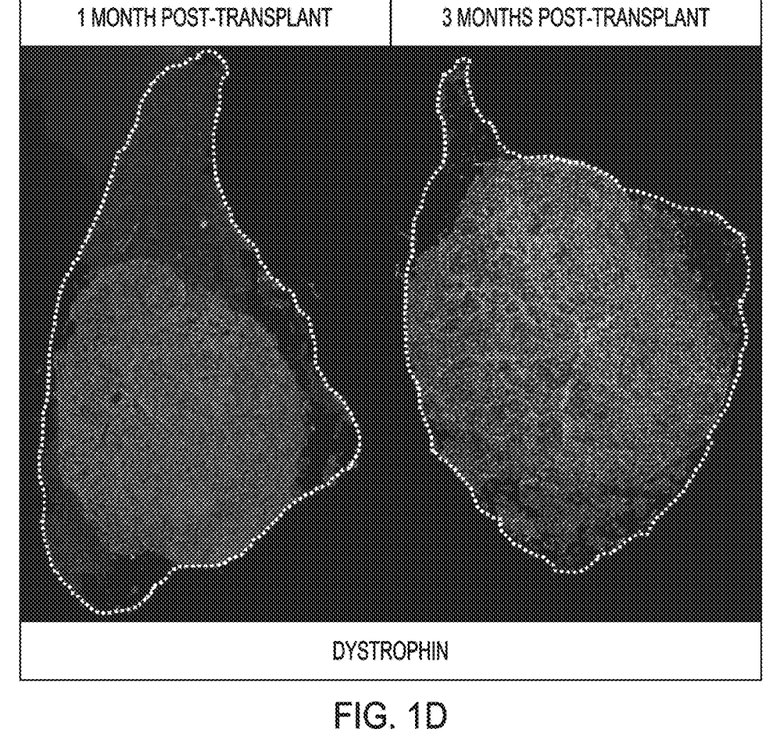
Figure 1E:
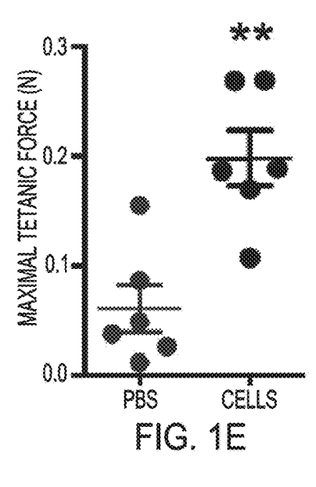
Figure 1F:
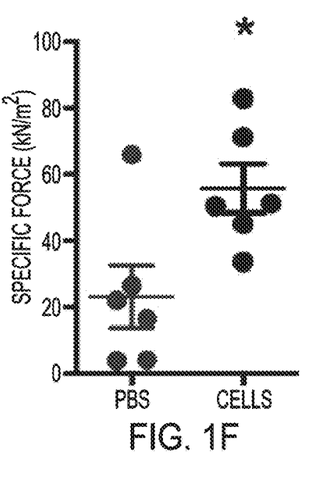
Figure 1G:
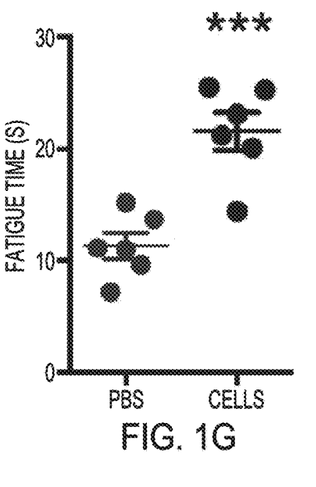
Figure 2A:
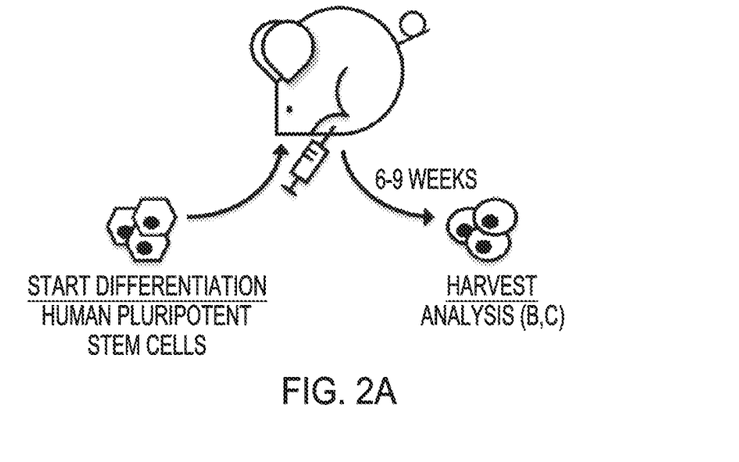
FIGS. 2A-G. Generation of skeletal myogenic progenitors/stem cells from human pluripotent stem cells. (A) Schematic of generating skeletal myogenic progenitors/stem cells from human pluripotent stem cells. (B-F) FACS profiling of 8 week-old teratomas. (G) Immunostaining reveals CD9+, CD29+, CD45+, CD73− and CD82+ fractions are myogenic (myosin heavy chain+).
Figure 2B:
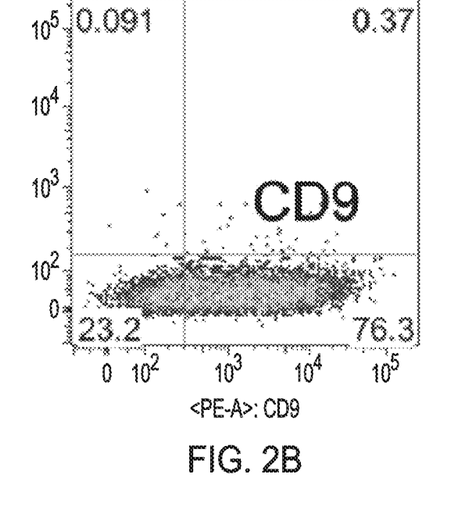
Figure 2C:
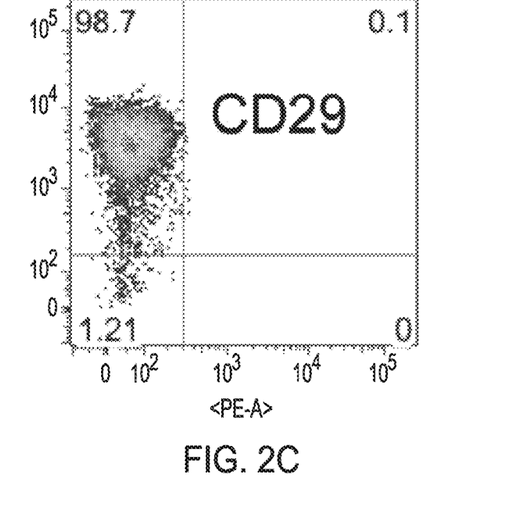
Figure 2D:
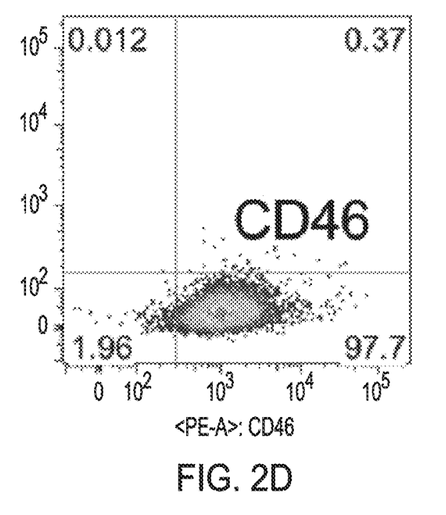
Figure 2E:
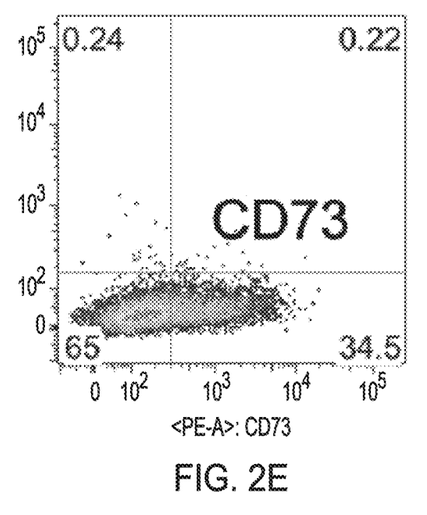
Figure 2F:
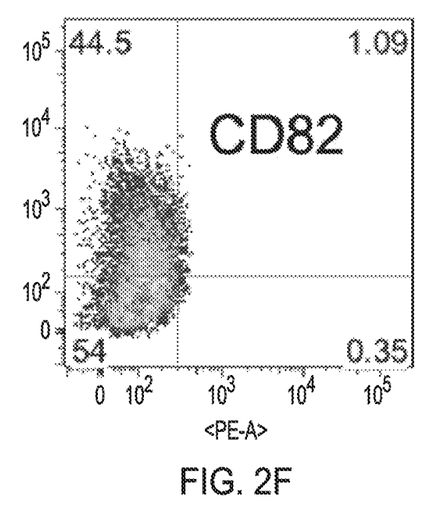
Figure 2G:
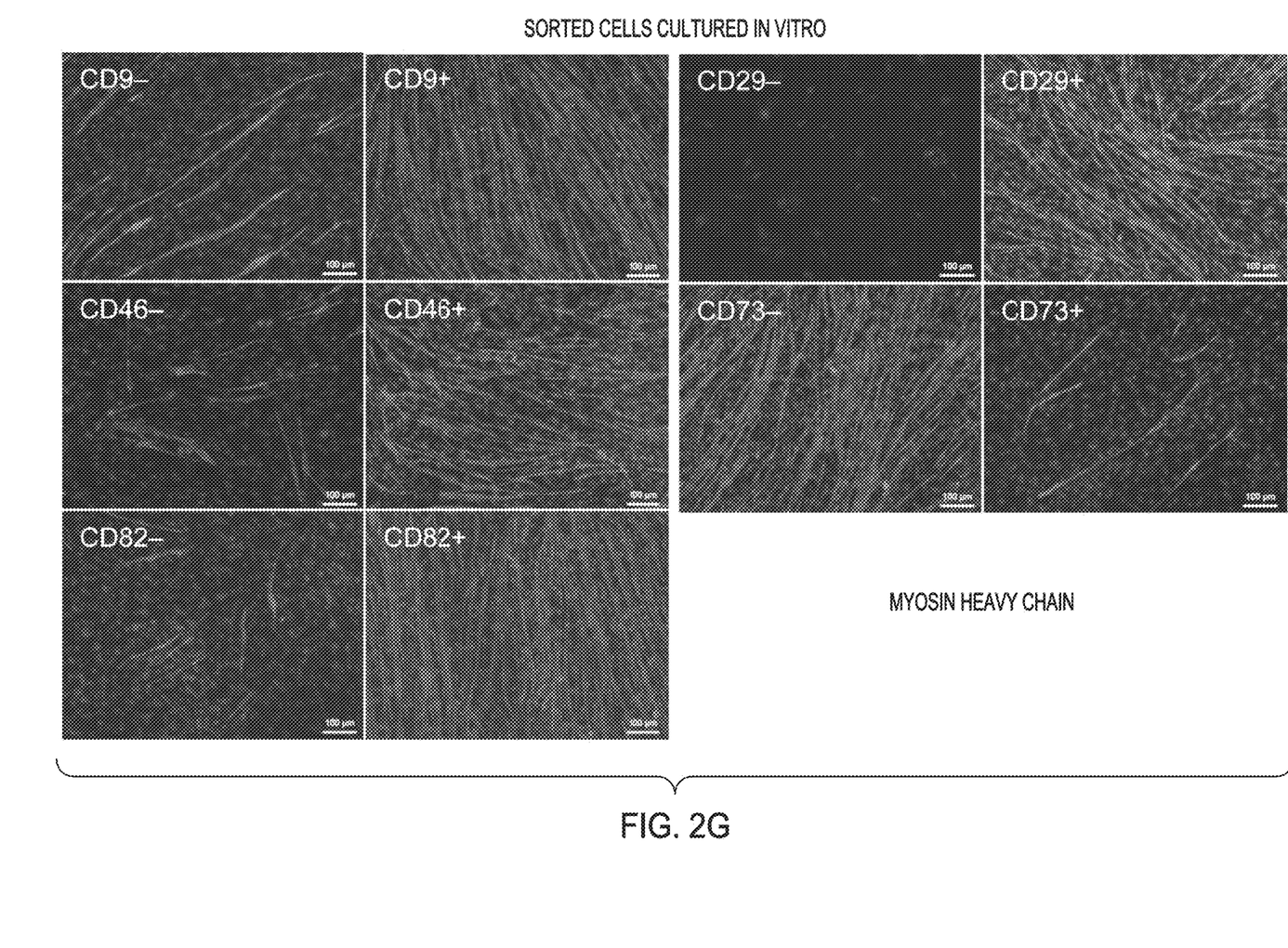

Herein, it is shown that teratomas derived from murine pluripotent stem cells produce large numbers of myogenic progenitors, and this is supported by their identification with the surface markers α7-Integrin and VCAM-1 in the mouse system and these or other markers as described, in the human system. Such progenitors can be FACS-purified using these or other markers, and then transplanted into diseased muscles, where they will give rise to unprecedented/surprising engraftment potential. In this system, 40,000 cells can reconstitute 70-80% of the tibialis anterior muscle volume. The new muscle tissue is functional, has greater force-generation potential compared to controls, and ameliorates dystrophy-related defects. These cells also contribute to a population of self-renewing PAX7+ muscle stem cells, which is beneficial in a cell therapy for muscle as they provide for long-term maintenance of the newly-formed muscle. Thus, therapeutically potent transplantable skeletal muscle stem cells can be generated by differentiating pluripotent stem cells into teratomas in vivo.

Definitions

In describing and claiming the invention, the following terminology will be used in accordance with the definitions set forth below. Unless defined otherwise, all technical and scientific terms used herein have the same meaning as commonly understood by one of ordinary skill in the art to which this invention belongs. Any methods and materials similar or equivalent to those described herein can be used in the practice or testing of the present invention. Specific and preferred values listed below for radicals, substituents, and ranges are for illustration only; they do not exclude other defined values or other values within defined ranges for the radicals and substituents.

As used herein, the articles "a" and "an" refer to one or to more than one, i.e., to at least one, of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

The term "isolated" refers to a factor(s), cell or cells which are not associated with one or more factors, cells or one or more cellular components that are associated with the factor(s), cell or cells in vivo.

"Cells" include cells from, or the "subject" is, a vertebrate, such as a mammal, including a human. Mammals include, but are not limited to, humans, farm animals, sport animals and companion animals. Included in the term "animal" is dog, cat, fish, gerbil, guinea pig, hamster, horse, rabbit, swine, mouse, monkey (e.g., ape, gorilla, chimpanzee, or orangutan), rat, sheep, goat, cow and bird.

"Progenitor cells" are cells produced during differentiation of a stem cell that have some, but not all, of the characteristics of their terminally differentiated progeny. Defined progenitor cells, such as "endothelial progenitor cells," are committed to a lineage, but not to a specific or terminally differentiated cell type.

"Self-renewal" refers to the ability to produce replicate daughter stem cells having differentiation potential that is identical to those from which they arose. A similar term used in this context is "proliferation."

"Expansion" refers to the propagation of a cell or cells without differentiation.

"Engraft" or "engrafiment" refers to the process of cellular contact and incorporation into an existing tissue of interest in vivo.

"Cytokines" refer to cellular factors that induce or enhance cellular movement, such as homing of stem cells, progenitor cells or differentiated cells. Cytokines may also stimulate such cells to divide.

"Differentiation factors" refer to cellular factors, preferably growth factors or factors that induce lineage commitment.

As used herein, "treat," "treating" or "treatment" includes treating, preventing, ameliorating, or inhibiting an injury or disease related condition and/or a symptom of an injury or disease related condition.

An "effective amount" generally means an amount which provides the desired local or systemic effect, such as enhanced performance. For example, an effective dose is an amount sufficient to affect a beneficial or desired clinical result. Said dose could be administered in one or more administrations and could include any preselected amount of cells. The precise determination of what would be considered an effective dose may be based on factors individual to each subject, including their size, age, injury and/or disease or being treated and amount of time since the injury occurred or the disease began. One skilled in the art, specifically a physician, would be able to determine the number of cells that would constitute an effective dose.

"Co-administer" can include simultaneous and/or sequential administration of two or more agents.

The terms "comprises," "comprising," and the like can have the meaning ascribed to them in U.S. Patent Law and can mean "includes," "including" and the like. As used herein, "including" or "includes" or the like means including, without limitation.

ASPECTS OF THE INVENTION

Compositions and methods of the invention are directed to the formation and use of teratoma-derived skeletal muscle stem cells. In one embodiment, the teratoma-derived skeletal muscle stem cells improve muscle contractile force (definition "functional") when administered to a patient in need thereof.

Muscle Diseases/Disorders

Muscles help you move and help your body work. Different types of muscles have different jobs. There are many problems that can affect muscles. Muscle disorders can cause weakness, pain or even paralysis.

Causes of muscle diseases/disorders include injury or overuse, such as sprains or strains, cramps or tendinitis, a genetic disorder, such as muscular dystrophy, cancer, inflammation, such as myositis, diseases of nerves that affect muscles, infections and certain medicines.

Myopathy is a muscular disease in which the muscle fibers do not function for any one of many reasons, resulting in muscular weakness. "Myopathy" simply means muscle disease (myo-Greek μν"muscle"+pathos-pathy Greek "suffering"). This meaning implies that the primary defect is within the muscle, as opposed to the nerves ("neuropathies" or "neurogenic" disorders) or elsewhere (e.g., the brain etc.). Muscle cramps, stiffness, and spasm can also be associated with myopathy.

Muscular disease can be classified as neuromuscular or musculoskeletal in nature. Some conditions, such as myositis, can be considered both neuromuscular and musculoskeletal.

Myopathies (also known as muscular dystrophy) in systemic disease results from several different disease processes including hereditary (presenting birth), endocrine, inflammatory (inflammatory myopathies caused by, for example, dermatomyositis, polymyositis; inclusion body myositis, viral (HIV)), paraneoplastic, infectious, drug- and toxin-induced (e.g., alcohol, corticosteroids, narcotics, colchicines, chloroquine), critical illness myopathy, metabolic, paraneoplastic myopathy, collagen related, and myopathies with other systemic disorders. Patients with systemic myopathies often present acutely or sub acutely. On the other hand, familial myopathies or dystrophies generally present in a chronic fashion with exceptions of metabolic myopathies where symptoms on occasion can be precipitated acutely. Most of the inflammatory myopathies can have a chance association with malignant lesions; the incidence appears to be specifically increased in patients with dermatomyositis.

There are many types of myopathy:

Inherited forms include: dystrophies ((or muscular dystrophies) are a subgroup of myopathies characterized by muscle degeneration and regeneration. Clinically, muscular dystrophies are typically progressive, because the muscles' ability to regenerate is eventually lost, leading to progressive weakness, often leading to use of a wheelchair, and eventually death, usually related to respiratory weakness), Myotonia, Neuromyotonia, congenital myopathies (which do not show evidence for either a progressive dystrophic process (i.e., muscle death) or inflammation, but instead characteristic microscopic changes are seen in association with reduced contractile ability of the muscles. Congenital myopathies include, but are not limited to: nemaline myopathy (characterized by presence of "nemaline rods" in the muscle), multi/minicore myopathy (characterized by multiple small "cores" or areas of disruption in the muscle fibers), centronuclear myopathy (or myotubular myopathy) (in which the nuclei are abnormally found in the center of the muscle fibers), a rare muscle wasting disorder), mitochondrial myopathies (which are due to defects in mitochondria, which provide a source of energy for muscle), familial periodic paralysis, inflammatory myopathies (which are caused by problems with the immune system attacking components of the muscle, leading to signs of inflammation in the muscle), metabolic myopathies (which result from defects in biochemical metabolism that primarily affect muscle), glycogen storage diseases (which may affect muscle) and/or lipid storage disorder.

Acquired forms include: External substance induced myopathy, Drug-induced myopathy, Glucocorticoid myopathy (is caused by this class of steroids increasing the breakdown of the muscle proteins leading to muscle atrophy), Alcoholic myopathy, Myopathy due to other toxic agents, dermatomyositis produces muscle weakness and skin changes; polymyositis produces muscle weakness, inclusion body myositis (is a slowly progressive disease that produces weakness of hand grip and straightening of the knees), Myositis ossificans, Rhabdomyolysis and/or myoglobinurias.

Teratoma-Derived Skeletal Muscle Stem Cells

Teratomas are differentiating masses that contain many cell types. They can be generated in the lab by implanting pluripotent cells (e.g., embryonic stem cells or induced pluripotent stem cells, iPSCs, which cells can be prepared and cultured by methods available to an art worker) into immune-deficient animals. The cells of the teratoma have a normal karyotype, therefore they are not cancerous, in spite of the "-oma" in the name. Herein it is shown that teratomas of mouse ES cells implanted into NSG mice contain skeletal muscle stem cells. Teratoma derived skeletal muscle stem cells appear to be of comparable regenerative potential to satellite cells, the adult stem cell for skeletal muscle.

Provided herein are pluripotent stem cell-derived teratomas rich in Lin− α7-integrin+ VCAM1+ (α7+ VCAM+) myogenic progenitors. Further provided is a method to reconstitute muscle in fiber in which as low as 40,000 α7+ VCAM+ cells reconstitute 70-80% of muscle fiber mass 3 months after transplantation. Additionally, new α7+ VCAM+ cell-derived fibers generate force and ameliorate dystrophin-related force deficiency. The α7+ VCAM+ cells mature into functional PAX7+ muscle stem cells in vivo. Thus, teratomas are a rich and accessible source of therapeutically potent transplantable skeletal muscle stem cells.

Briefly, and as further discussed below, the method involves: 1) generate teratoma in an immunodeficient animal (e.g., immunedeficient mice or pigs); 2) harvest teratoma 1-2 months later; 3) isolate skeletal muscle stem cells using a cocktail of surface markers for positive/negative selection, for example, for mouse stem cells, use: CD45-neg CD31-neg VCAM1+ Itga7+ and for human stem cells, use: CD45-neg CD31-neg CD56+; human cells can also use CD9+, CD29+, CD46+, CD73−, CD82+ or a combination thereof; and 4) transplant these stem cells into injured or diseased muscle. It is currently beyond the state of the art to generate functional skeletal muscle stem cells from wild-type (unmodified) pluripotent cells. With the process provided herein, it is shown that teratoma-derived skeletal muscle stem cells are able to improve muscle contractile force (definition "functional").

Administer Cells

The cells prepared as described herein can be administered to a subject by a variety of methods available to the art, including but not limited to localized injection, catheter administration, systemic injection, intraperitoneal injection, parenteral administration, intra-arterial injection, intravenous injection, intraventricular infusion, intraplacental injection, intrauterine injection, surgical intramyocardial injection, transendocardial injection, transvascular injection, intracoronary injection, transvascular injection, intramuscular injection, surgical injection into a tissue of interest or via direct application to tissue surfaces (e.g., during surgery or on a wound).

Intravenous injection is the simplest method of cell administration; however a greater degree of dependence on homing of the stem cells is required for them to reach the tissue of interest. "Homing" of the cells to the injured tissues would concentrate the implanted cells in an environment favorable to their growth and function. Pre-treatment of a patient with cytokine(s) to promote homing is another alternative contemplated in the methods of the present invention. Where homing signals may be less intense, injection of the cells directly into the muscle can produce a more favorable outcome. Certain cytokines (e.g., cellular factors that induce or enhance cellular movement, such as homing of stem cells, progenitor cells or differentiated cells) can enhance the migration of cells or their differentiated counterparts to the site of damaged muscle tissue. Cytokines include, but are not limited to, stromal cell derived factor-1 (SDF-1), stem cell factor (SCF) and granulocyte-colony stimulating factor (G-CSF). Cytokines also include any which promote the expression of endothelial adhesion molecules, such as ICAMs, VCAMs, and others, which facilitate the homing process.

Viability of newly forming tissues can be enhanced by angiogenesis. Factors promoting angiogenesis include but are not limited to VEGF, aFGF, angiogenin, angiotensin-1 and -2, betacellulin, bFGF, Factor X and Xa, HB-EGF, PDGF, angiomodulin, angiotropin, angiopoetin-1, prostaglandin E1 and E2, steroids, heparin, 1-butyryl-glycerol, nicotinic amide.

Factors that decrease apoptosis can also promote the formation of new tissue, such as muscle. Factors that decrease apoptosis include but are not limited to β-blockers, angiotensin-converting enzyme inhibitors (ACE inhibitors), AKT, HIF, carvedilol, angiotensin II type 1 receptor antagonists, caspase inhibitors, cariporide, and eniporide.

Exogenous factors (e.g., cytokines, differentiation factors (e.g., cellular factors, such as growth factors or angiogenic factors that induce lineage commitment), angiogenesis factors and anti-apoptosis factors) can be administered prior to, after or concomitantly with the skeletal muscle cells. Doses for administration(s) are variable and may include an initial administration followed by subsequent administrations.

In current human studies of autologous mononuclear bone marrow cells, empirical doses ranging from 1 to $4\times10^7$ cells have been used. However, different scenarios may require optimization of the amount of cells injected into a tissue of interest. Thus, the quantity of cells to be administered will vary for the subject being treated. In one embodiment, between $10^4$ to $10^8$, more preferably $10^5$ to $10^7$, and most preferably, $3\times10^7$ stem cells and optionally, 50 to 500 µg/kg per day of a cytokine can be administered to a human subject. For local muscle placement/injection, as few as 40,000 cells can be administered. However, the precise determination of what would be considered an effective dose may be based on factors individual to each patient, including their size, age, disease or injury, size damage, amount of time since the damage occurred and factors associated with the mode of delivery (direct injection—lower doses, intravenous—higher doses).

The skilled artisan can readily determine the amount of cells and optional additives, vehicles, and/or carrier in compositions and to be administered in methods of the invention. Typically, any additives (in addition to the active cell(s) and/or cytokine(s)) are present in an amount of 0.001 to 50 wt % solution in phosphate buffered saline, and the active ingredient is present in the order of micrograms to milligrams, such as about 0.0001 to about 5 wt %, including about 0.0001 to about 1 wt %, including about 0.0001 to about 0.05 wt % or about 0.001 to about 20 wt %, including about 0.01 to about 10 wt %, and including about 0.05 to about 5 wt %. Of course, for any composition to be administered to an animal or human, and for any particular method of administration, it is preferred to determine therefore: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable response.

When administering a therapeutic composition of the present invention, it will generally be formulated in a unit dosage injectable form (solution, suspension, emulsion). The pharmaceutical formulations suitable for injection include sterile aqueous solutions and dispersions. The carrier can be a solvent or dispersing medium containing, for example, water, saline, phosphate buffered saline, polyol (for example, glycerol, propylene glycol, liquid polyethylene glycol, and the like) and suitable mixtures thereof.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the cells.

Sterile injectable solutions can be prepared by incorporating the cells utilized in practicing the present invention in the required amount of the appropriate solvent with various amounts of the other ingredients, as desired.

In one embodiment, the cells can be administered initially, and thereafter maintained by further administration of the cells. For instance, the cells can be administered by one method of injection, and thereafter further administered by a different or the same type of method. For example, cells can be administered by surgical injection to bring muscle function to a suitable level. The patient's levels can then be maintained, for example, by intravenous injection, although other forms of administration, dependent upon the patient's condition, can be used.

It is noted that human subjects are treated generally longer than the canines or other experimental animals, such that treatment has a length proportional to the length of the disease process and effectiveness. The doses may be single doses or multiple doses over a period of several days. Thus, one of skill in the art can scale up from animal experiments, e.g., rats, mice, canines and the like, to humans, by techniques from this disclosure and documents cited herein and the knowledge in the art, without undue experimentation. The treatment generally has a length proportional to the length of the disease process and drug effectiveness and the subject being treated.

Examples of compositions comprising the cells of the invention include liquid preparations for administration, including suspensions; and, preparations for direct or intravenous administration (e.g., injectable administration), such as sterile suspensions or emulsions. Such compositions may be in admixture with a suitable carrier, diluent, or excipient such as sterile water, physiological saline, glucose, dextrose, or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Compositions of the invention are conveniently provided as liquid preparations, e.g., isotonic aqueous solutions, suspensions, emulsions or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues.

The choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Solutions, suspensions and gels normally contain a major amount of water (preferably purified, sterilized water) in addition to the cells. Minor amounts of other ingredients such as pH adjusters (e.g., a base such as NaOH), emulsifiers or dispersing agents, buffering agents, preservatives, wetting agents and jelling agents (e.g., methylcellulose), may also be present. The compositions can be isotonic, i.e., they can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected and the desired viscosity. Viscous compositions are normally prepared from solutions by the addition of such thickening agents.

A pharmaceutically acceptable preservative or cell stabilizer can be employed to increase the life of the compositions. Preferably, if preservatives are necessary, it is well within the purview of the skilled artisan to select compositions that will not affect the viability or efficacy of the cells as described in the present invention.

Compositions can be administered in dosages and by techniques available to those skilled in the medical and veterinary arts taking into consideration such factors as the age, sex, weight, and condition of the particular patient, and the composition form used for administration (e.g., solid vs. liquid).

Suitable regimes for initial administration and further doses or for sequential administrations also are variable, may include an initial administration followed by subsequent administrations.

The following example is intended to further illustrate certain particularly preferred embodiments of the invention and are not intended to limit the scope of the invention in any way.

EXAMPLE

Regenerative therapy for muscle damage or diseases, i.e. muscular dystrophy.

Introduction

Muscle stem cells express the transcription factor PAX7 and are the primary cell type responsible for regeneration of muscle after injury and maintenance throughout life (Gunther et al., 2013; Seale et al., 2000; von Maltzahn et al., 2013). Muscle stem cells are rare in adult muscle, comprising only 1-2% of the mononuclear fraction (Bosnakovski et al., 2008). Satellite cells in normal healthy muscle reside under the fiber basal lamina (Mauro, 1961), and methods of isolation require the muscle tissue containing them to be removed from the donor, therefore in humans, only relatively small biopsies are possible. Satellite cells have considerable regenerative potential (Arpke et al., 2013; Collins et al., 2005; Hall et al., 2010; Sacco et al., 2008), however the small cell number that can be isolated from a biopsy is not sufficient to enable the regeneration of a significant amount of muscle. Although satellite cells will divide and their progeny will proliferate when placed into in vitro culture, these cultured cells are no longer the same as satellite cells, and their transplantation potential is very limited (Gussoni et al. 1992; Mendell et al., 1995; Montarras et al. 2005; Sacco et al. 2008). Embryonic stem (ES) cells and induced pluripotent stem (iPS) cells have been considered as a source of material for muscle cell transplantation, however they are difficult to differentiate into muscle in vitro and although some protocols have been published to derive skeletal myotubes from pluripotent cells in vitro (Chal et al., 2015; Shelton et al., 2014), transplantable cells that can give rise to meaningful muscle grafts, i.e. grafts capable of generating a measurable difference in force produced have only been derived from pluripotent cells that have been geneticly modified to overexpress PAX3 (Darabi et al., 2008; Filareto et al., 2013) or PAX7 (Darabi et al., 2012).

In the development of the embryo, the skeletal muscle derives from a very complex process, involving precisely-timed cell movements, patterning by morphogens produced by various embryonic structures, and migration of muscle stem cell away from sites where they were produced. In vitro methods of differentiation have not yet been able to replicate this complexity, however teratomas that grow up in host animals from implanted pluripotent stem cells often contain highly complex tissues such as hair follicles, glands, and other structures. Therefore teratomas were evaluated for the presence of skeletal muscle progenitors.

Materials and Methods

E14-GFP ES cells (Ismailoglu et al., 2008) were cultured in maintenance medium (Knock-Out Dulbecco's Minimum Essential Medium (DMEM) (Life Technologies, Grand Island, N.Y.), 15% ES cells-qualified fetal bovine serum (ES-FBS) (Gemini Bio-Products, West Sacramento, Calif.), 1% non-essential amino acids (NEAA) (Life Technologies), 1% penicillin/streptomycin (P/S) (Life Technologies), 2 mM Glutamax (Life Technologies), 0.1 mM β-mercaptoethanol (Sigma, St. Louis, Mo.) and 500 U/ml leukemia inhibitory factor (Millipore, Temecula, Calif.)) on irradiated embryonic fibroblasts at 37° C. in 5% $CO_2$. To generate teratomas, MEFs were removed by first trypsinizing ES cells and then plating on a cell culture flask for 60 min. Human pluripotent stem cells were maintained in Geltrex-coated flask in TeSR-E8 medium (Stem Cell Technologies, Canada).

Myogenic differentiation was initiated by culturing FACS-sorted cells in myogenic medium: DMEM/F12 (Life Technologies), 20% FBS (HyClone, Logan, Utah), 10% horse serum (HyClone), basic FGF (10 ng/ml, R&D Systems, Minneapolis, Minn.), 1% P/S and 2 mM Glutamax. Myogenic cells were defined as MHC+ by immunostaining after 8 days of culture.

For FACS analysis and cell sorting, antibodies were added to dissociated cells for 30 min on ice. Propidium iodide (PI) (1 µg/ml, Sigma) was added to separate live (PI−) and dead cells (PI+). A BD FACSAriaII (BD Biosciences, San Diego, Calif.) with a 4-way purity precision setting was used. FlowJo (Tree Star, Ashland, Oreg.) was used for data analysis.

Antibodies used are listed in Table 1.

TABLE 1

List of primary antibodies:

| Antigen | Conjugation | Vendor |
| --- | --- | --- |
| a7-Integrin | APC | AbLab (Vancouver, Canada) |
| CD31 | PE-Cy7 | BD Biosciences (San Jose, CA) |
| CD45 | PE-Cy7 | BD Biosciences |
| Dystrophin | Unconjugated | Abcam (Cambridge, MA) |
| Pax7 | Unconjugated | Developmental Studies Hybridoma Banks (Iowa City, IA) |
| Sarcomeric myosin heavy chain (MHC) | Unconjugated | Developmental Studies Hybridoma Banks |
| VCAM-1 | Biotin | eBioscience (San Diego, CA) |
| CD9 | PE | R&D Systems (Minneapolis, MN) |
| CD29 | APC | R&D Systems |
| CD46 | PE | R&D Systems |
| CD73 | PE | R&D Systems |
| CD82 | APC | R&D Systems |

For immunostaining, cells were first fixed with 4% paraformaldehyde (PFA) (Sigma) for 60 min, followed by 0.3% Triton X-100 (Sigma) for 30 min and 3% bovine serum albumin (BSA) (Sigma) for 1 hr in room temperature. Cells were incubated with primary antibodies overnight at 4° C. and then secondary antibodies (Alexa Fluor-488 or -555 conjugated) (Life Technologies) for 60 min at room temperature.

For cell transplantation, 4 month-old NSG-mdx4Cv mice were used (Arpke et al., 2013). Recipient mice were anesthetized with ketamine and xylazine. Two days prior to cell transplantation, a dose of 1200 cGy was used to irradiate the hind limbs using an X-RAD 320 irradiator (Precision X-Ray, North Branford, Conn.). On the next day, injury to the TA muscle was induced by a single dose of 10 uM cardiotoxin (Calbiochem, La Jolla, Calif.). For generate teratoma, 250.000 mouse pluripotent cells or 1,000,000 human pluripotent cells were injected using a Hamilton syringe. For myogenic progenitor transplantation, 40,000 Lin− α7+ VCAM+ cells were injected to irradiated and cardiotoxin-injured TAs. TAs were harvested 3-4 weeks (mouse teratomas), 6-9 weeks (human teratomas) or 1-3 months later (myogenic progenitors) after transplantation for analysis. In vitro physiological evaluation of transplanted TAs was described previously (Arpke et al. 2013).

Values shown represent mean ±SEM. Student's t-test or one-way ANOVA followed by Tukey post-hoc test were used for comparison of groups (two or more than two groups, respectively) with statistical significance considered when $p<0.05$.

Experimental Results

Teratomas Contain Myogenic Progenitors, and these are Marked by a 7-Integrin and VCAM-1

EGFP+ murine ES cells (Ismailoglu et al., 2008) were injected into injured, irradiated tibialis anterior (TA) muscles of NSG-mdx4Cv mice, in order to maximize the exposure of teratomas cells to myogenic factors. NSG-mdx4Cv mice are immune- and dystrophin-deficient, thus they allow robust engraftment, as well as unequivocal identification of donor-derived (DYSTROPHIN+) muscle tissue (Arpke et al., 2013). Hind limbs were irradiated prior to implantation, in order to reduce competition with host satellite cells, and following irradiation, cardiotoxin was injected into TA muscles to stimulate myogenesis. Three weeks after implantation, teratomas were harvested, cells disaggregated and subjected to flow cytometry. Cells bearing the hematopoietic and endothelial markers CD45 and PECAM (Lin−) were excluded and cells expressing the satellite cell markers α7-integrin and VCAM-1 were included (Blanco-Bose et al., 2001; Chan et al., 2013; Fukada et al., 2007; Jesse et al., 1998; Seale et al., 2004). Cells so gated represented about 10% of the total Lin− fraction. When plated into culture, they could differentiate into myosin heavy chain (MHC)+ myotubes. These cells were cytospun and slides were s immunostained with PAX7 antibody, which revealed that about 30% of cells expressed PAX7, which is a marker for muscle stem cells.

Myogenic Progenitors from Teratomas have Unexpectedly Tremendous Regenerative Potential 40,000 α7+ VCAM+ cells were sorted and transplanted into TA muscles of a second set of NSG-mdx4Cv recipient mice. Prior studies involving myoblast transplantation (Partridge et al., 1989) or ES cells genetically modified to overexpress PAX3 or PAX7 (Darabi et al., 2008) have used tremendously higher numbers of cells. One month post-transplant regeneration was evaluated by isolating TA muscles, preparing frozen sections, and immunostaining with Dystrophin antibody, to recognize donor-derived myofibers. Regeneration was observed on a scale that surpasses what has previously been documented. By one month post-transplant, about ⅔ of the TA muscle was composed of donor-derived fibers, and this number went up to about 80% by 3 months.

It was next tested whether the newly-formed muscle fibers were functional by measuring the transplanted muscles' force generation ex vivo. This revealed that transplanted muscles were about 3 times stronger than the sham contralateral controls, demonstrating that the new muscle fibers are capable of generating force when electrically stimulated. The specific force (maximal force normalized to the size of the muscle) was also much increased. Specific force is a quality of force metric that is lower in DYSTROPHIN-deficient muscle, due to the disease. It was found that muscles transplanted with teratome-derived muscle progenitors showed increased specific force. Dystrophic muscle is also more fatigable than normal muscle. Muscles transplanted with teratome-derived muscle progenitors showed lower fatigability than contralateral controls. These results shows that the transplantation ameliorated features of the disease.

Myogenic progenitors in human teratomas are CD9+, CD29+, CD46+, CD73− and CD82+

To test whether the method of generating myogenic progenitors is extendable to human pluripotent stem cells, undifferentiated human pluripotent stem cells were injected into the TAs of NSG-mdx4Cv mice to form teratomas. After 6-9 weeks, teratomas were harvested and then analyzed by FACS. Teratoma cells were screened with a panel of antibodies, and various fractions were sorted and cultured in myogenic medium. It was discovered that human pluripotent stem cell-derived teratomas indeed harbor a myogenic progenitor population that is CD9+, CD29+, CD46+, CD73− and CD82+.

These results show that teratoma-derived cells can be applied to human cell therapy. To apply this method to the humans, teratomas can be generated in a larger animal model, such as an immunodeficient Rag2 pig (Lee et al., 2014). The concern that teratoma-derived cells could generate new teratomas in recipients was set to rest in the study herein, as no teratomas were seen in mice transplanted with teratomas-derived cells that had been sorted using specific surface markers, even out to 9 months post-transplantation.

The ability of teratomas-derived myogenic progenitors to generate functional, force generating, skeletal muscle tissue in vivo, is unrivaled to date. Differentiation via teratoma, which is much less labor-intensive and costly than conventional in vitro tissue culture differentiation, and more effective at generating functional skeletal muscle progenitors, is thus a preferred method of producing therapeutic myogenic progenitor cells.

BIBLIOGRAPHY

Arpke, R. W., Darabi. R., Mader. T. L., Zhang, Y., Toyama, A., Lonetree. C. L., Nash, N., Lowe. D. A., Perlingeiro, R. C., and Kyba, M. (2013). A New Immuno-Dystrophin-Deficient Model, the NSG-Mdx Mouse, Provides Evidence for Functional Improvement Following Allogeneic Satellite Cell Transplantation. Stem Cells.

Blanco-Bose, W. E., Yao, C. C., Kramer. R. H., and Blau, H. M. (2001). Purification of mouse primary myoblasts based on alpha 7 integrin expression. Exp Cell Res 265, 212-220.

Bober, E., Franz, T., Arnold. H. H., Gruss, P., and Tremblay, P. (1994). Pax-3 is required for the development of limb muscles: a possible role for the migration of dermomyotomal muscle progenitor cells. Development 120, 603-612.

Bosnakovski, D., Xu, Z., Li, W., Thet, S., Cleaver, O., Perlingeiro, R. C., and Kyba, M. (2008). Prospective isolation of skeletal muscle stem cells with a Pax7 reporter. Stem Cells 26, 3194-3204.

Brack, A. S., Bildsoe, H., and Hughes, S. M. (2005). Evidence that satellite cell decrement contributes to preferential decline in nuclear number from large fibres during murine age-related muscle atrophy. Journal of cell science 118, 4813-4821.

Chal, J., Oginuma, M., Al Tanoury, Z., Gobert, B., Sumara, O., Hick, A., Bousson, F., Zidouni, Y., Mursch, C., Moncuquet, P., et al. (2015). Differentiation of pluripotent stem cells to muscle fiber to model Duchenne muscular dystrophy. Nat Biotechnol.

Chan, S. S., Shi, X., Toyama, A., Arpke, R. W., Dandapat, A., Iacovino, M., Kang, J., Le, G., Hagen, H. R., Garry, D. J., et al. (2013). Mesp1 patterns mesoderm into cardiac, hematopoietic, or skeletal myogenic progenitors in a context-dependent manner. Cell Stem Cell 12, 587-601.

Collins, C. A., Olsen, I., Zammit, P. S., Heslop, L., Petrie, A., Partridge, T. A., and Morgan, J. E. (2005). Stem cell function, self-renewal, and behavioral heterogeneity of cells from the adult muscle satellite cell niche. Cell 122, 289-301.

Darabi, R., Arpke, R. W., Irion, S., Dimos, J. T., Grskovic, M., Kyba, M., and Perlingeiro, R. C. (2012). Human ES- and iPS-derived myogenic progenitors restore dystrophin and improve contractility upon transplantation in dystrophic mice. Cell Stem Cell 10, 610-619.

Darabi, R., Gehlbach, K., Bachoo, R. M., Kamath, S., Osawa, M., Kamm, K. E., Kyba, M., and Perlingeiro, R. C. (2008). Functional skeletal muscle regeneration from differentiating embryonic stem cells. Nature medicine 14, 134-143.

Eventov-Friedman, S., Katchman, H., Shezen, E., Aronovich, A., Tchorsh, D., Dekel, B., Freud, E., and Reisner, Y. (2005). Embryonic pig liver, pancreas, and lung as a source for transplantation: optimal organogenesis without teratoma depends on distinct time windows. Proceedings of the National Academy of Sciences of the United States of America 102, 2928-2933.

Filareto, A., Parker, S., Darabi, R., Borges, L., Iacovino, M., Schaaf, T., Mayerhofer, T., Chamberlain, J. S., Ervasti, J. M., Mclvor, R. S., et al. (2013). An ex vivo gene therapy approach to treat muscular dystrophy using inducible pluripotent stem cells. Nat Commun 4, 1549.

Fukada, S., Uezumi, A., Ikemoto, M., Masuda, S., Segawa, M., Tanimura, N., Yamamoto, H., Miyagoe-Suzuki, Y., and Takeda, S. (2007). Molecular signature of quiescent satellite cells in adult skeletal muscle. Stem Cells 25, 2448-2459.

Goulding, M., Lumsden, A., and Paquette, A. J. (1994). Regulation of Pax-3 expression in the dermomyotome and its role in muscle development. Development 120, 957-971.

Gunther, S., Kim, J., Kostin, S., Lepper, C., Fan, C. M., and Braun, T. (2013). Myf5-positive satellite cells contribute to Pax7-dependent long-term maintenance of adult muscle stem cells. Cell Stem Cell 13, 590-601.

Gussoni, E., Pavlath, G. K., Lanctot, A. M., Sharma. K. R., Miller. R. G., Steinman, L., and Blau, H. M. (1992). Normal dystrophin transcripts detected in Duchenne muscular dystrophy patients after myoblast transplantation. Nature 356, 435-438.

Hall, J. K., Banks, G. B., Chamberlain, J. S., and Olwin, B. B. (2010). Prevention of muscle aging by myofiber-associated satellite cell transplantation. Sci Transl Med 2, 57ra83.

Ismailoglu, I., Yeamans, G., Daley, G. Q., Perlingeiro, R. C., and Kyba, M. (2008). Mesodermal patterning activity of SCL. Exp Hematol 36, 1593-1603.

Jesse, T. L., LaChance, R., Iademarco, M. F., and Dean, D. C. (1998). Interferon regulatory factor-2 is a transcriptional activator in muscle where It regulates expression of vascular cell adhesion molecule-1. J Cell Biol 140, 1265-1276.

Kuang, S., Charge, S. B., Seale, P., Huh, M., and Rudnicki, M. A. (2006). Distinct roles for Pax7 and Pax3 in adult regenerative myogenesis. J Cell Biol 172, 103-113.

Kyba, M., Perlingeiro, R. C. R., and Daley, G. Q. (2002). HoxB4 confers definitive lymphoid myeloid engraftment potential on embryonic stem cell and yolk sac hematopoietic progenitors. Cell 109, 29-37.

Lee, K., Kwon, D. N., Ezashi, T., Choi, Y. J., Park, C., Ericsson, A. C., Brown, A. N., Samuel, M. S., Park, K. W., Walters, E. M., et al. (2014). Engraftment of human iPS cells and allogeneic porcine cells into pigs with inactivated RAG2 and accompanying severe combined immunodeficiency. Proceedings of the National Academy of Sciences of the United States of America 111, 7260-7265.

Mauro, A. (1961). Satellite cell of skeletal muscle fibers. J Biophys Biochem Cytol 9, 493-495. Mendell, J. R., Kissel, J. T., Amato, A. A., King, W., Signore, L., Prior, T. W., Sahenk, Z., Benson, S., McAndrew, P. E., Rice, R., et al. (1995). Myoblast transfer in the treatment of Duchenne's muscular dystrophy. N Engl J Med 333, 832-838.

Montarras, D., Morgan, J., Collins, C., Relaix, F., Zaffran, S., Cumano, A., Partridge, T., and Buckingham, M. (2005). Direct isolation of satellite cells for skeletal muscle regeneration. Science 309, 2064-2067.

Partridge, T. A., Morgan, J. E., Coulton, G. R., Hoffman, E. P., and Kunkel, L. M. (1989). Conversion of mdx myofibres from dystrophin-negative to -positive by injection of normal myoblasts. Nature 337, 176-179.

Perlingeiro, R. C. R., Kyba, M., and Daley, G. Q. (2001). Clonal analysis of differentiating embryonic stem cells reveals a hematopoietic progenitor with primitive erythroid and adult lymphoid-myeloid potential. Development 128, 4597-4604.

Sacco, A., Doyonnas, R., Kraft, P., Vitorovic, S., and Blau, H. M. (2008). Self-renewal and expansion of single transplanted muscle stem cells. Nature.

Seale, P., Ishibashi, J., Holterman. C., and Rudnicki, M. A. (2004). Muscle satellite cell-specific genes identified by genetic profiling of MyoD-deficient myogenic cell. Dev Biol 275, 287-300.

Scale, P., Sabourin, L. A., Girgis-Gabardo, A., Mansouri, A., Gruss, P., and Rudnicki, M. A. (2000). Pax7 is required for the specification of myogenic satellite cells. Cell 102, 777-786.

Shelton, M., Metz, J., Liu, J., Carpenedo, R. L., Demers, S. P., Stanford, W. L., and Skerjanc, I. S. (2014). Derivation and expansion of PAX7-positive muscle progenitors from human and mouse embryonic stem cells. Stem Cell Reports 3, 516-529.

Takahashi, K., and Yamanaka. S. (2006). Induction of pluripotent stem cells from mouse embryonic and adult fibroblast cultures by defined factors. Cell 126, 663-676.

von Maltzahn, J., Jones, A. E., Parks, R. J., and Rudnicki, M. A. (2013). Pax7 is critical for the normal function of satellite cells in adult skeletal muscle. Proceedings of the National Academy of Sciences of the United States of America 110, 16474-16479.

Arpke, R. W., Darabi. R., Mader. T. L., Zhang, Y., Toyama, A., Lonetree, C. L., Nash, N., Lowe. D. A., Perlingeiro, R. C., and Kyba, M. (2013). A New Immuno-Dystrophin-Deficient Model, the NSG-Mdx Mouse, Provides Evidence for Functional Improvement Following Allogeneic Satellite Cell Transplantation. Stem Cells.

Bosnakovski, D., Xu, Z., Li, W., Thet, S., Cleaver, O., Perlingeiro, R. C., and Kyba. M. (2008). Prospective isolation of skeletal muscle stem cells with a Pax7 reporter. Stem Cells 26, 3194-3204.

Ismailoglu, I., Yeamans, G., Daley, G. Q., Perlingeiro, R. C., and Kyba, M. (2008). Mesodermal patterning activity of SCL. Exp Hematol 36, 1593-1603.

Takahashi, K., and Yamanaka, S. (2006). Induction of pluripotent stem cells from mouse embryonic and adult fibroblast cultures by defined factors. Cell 126, 663-676.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An isolated skeletal muscle stem cell that does not comprise a genetic modification of Pax3 and wherein 40,000 of said stem cells, upon injection into a tibialis anterior muscle, can reconstitute 70-80% of said muscle volume and is produced by:
   a) injecting pluripotent stem cells into an immunodeficient animal,
   b) allowing one or more teratomas to form in said animal of a), and
   c) isolating said skeletal muscle stem cells from the one or more teratomas of b).

2. Isolated teratoma derived skeletal muscle stem cells that are Lin– α7-integrin+ VCAM1+(α7+ VCAM) and have no genetic modification of Pax3, wherein 40,000 of said stem cells, upon injection into a tibialis anterior muscle can reconstitute 70-80% of said muscle volume.

3. Isolated teratoma derived skeletal muscle stem cells that are CD45-neg CD31-neg VCAM1+Itga7+ or CD45-neg CD31-neg CD56+ and have no genetic modification of Pax3, wherein 40,000 of said stem cells, upon injection into a tibialis anterior muscle can reconstitute 70-80% of said muscle volume.

4. Isolated teratoma derived skeletal muscle stem cells that are CD9+, CD29+, CD46+, CD73–, CD82+ or a combination thereof and have no genetic modification of Pax3, wherein 40,000 of said stem cells, upon injection into a tibialis anterior muscle can reconstitute 70-80% of said muscle volume.

* * * * *

UNITED STATES PATENT AND TRADEMARK OFFICE
CERTIFICATE OF CORRECTION

PATENT NO. : 11,306,287 B1
APPLICATION NO. : 15/625619
DATED : April 19, 2022
INVENTOR(S) : Kyba et al.

It is certified that error appears in the above-identified patent and that said Letters Patent is hereby corrected as shown below:

On the Title Page

In Column 2, Item (56) under "Other Publications", Line 16, delete "Ceil" and insert --Cell-- therefor In Column 2, Item (56) under "Other Publications", Line 17, delete "Ef?cacy" and insert --Efficacy-- therefor In the Specification In Column 4, Line 26, delete "arc" and insert --are-- therefor In Column 4, Line 43, delete ""engrafiment"" and insert --"engraftment"-- therefor In Column 5, Line 25, delete "tendinitis," and insert --tendinitis;-- therefor In Column 5, Line 32, delete "μv" and insert --μυo-- therefor In Column 6, Line 40, delete "arc" and insert --are-- therefor In Column 6, Line 46, delete "arc" and insert --are-- therefor In Column 11, table 1, Line 42, delete "a7-Integrin" and insert --α7-Integrin-- therefor In Column 12, Line 7, delete "uM" and insert --μM-- therefor Signed and Sealed this
Twenty-second Day of November, 2022

Katherine Kelly Vidal
*Director of the United States Patent and Trademark Office*